(12) United States Patent
Reddy et al.

(10) Patent No.: US 7,094,903 B2
(45) Date of Patent: *Aug. 22, 2006

(54) PROCESSES FOR THE PREPARATION OF SUBSTITUTED ISOXAZOLES AND 2-ISOXAZOLINES

(75) Inventors: M. V. Ramana Reddy, Upper Darby, PA (US); Stanley C. Bell, Narberth, PA (US)

(73) Assignee: Onconova Therapeutics, Inc., Lawrenceville, NJ (US)

( * ) Notice: Subject to any disclaimer, the term of this patent is extended or adjusted under 35 U.S.C. 154(b) by 28 days.

This patent is subject to a terminal disclaimer.

(21) Appl. No.: 10/960,397

(22) Filed: Oct. 7, 2004

(65) Prior Publication Data

US 2005/0143583 A1 Jun. 30, 2005

Related U.S. Application Data

(62) Division of application No. 10/269,559, filed on Oct. 11, 2002, now Pat. No. 6,809,204.

(60) Provisional application No. 60/328,901, filed on Oct. 12, 2001.

(51) Int. Cl.
C07D 261/04 (2006.01)

(52) U.S. Cl. .................................................. 548/240

(58) Field of Classification Search ................ 548/240
See application file for complete search history.

(56) References Cited

U.S. PATENT DOCUMENTS

| | | | | |
|---|---|---|---|---|
| 5,563,165 | A | 10/1996 | Talley et al. | 514/406 |
| 5,604,253 | A | 2/1997 | Lau et al. | 514/415 |
| 5,908,852 | A | 6/1999 | Talley et al. | 514/340 |
| 5,932,598 | A | 8/1999 | Talley et al. | 514/341 |
| 5,972,986 | A | 10/1999 | Seibert et al. | 514/406 |
| 6,025,353 | A | 2/2000 | Masferrer et al. | 514/210 |
| 6,376,519 | B1 | 4/2002 | Reddy et al. | 514/341 |
| 6,579,988 | B1 | 6/2003 | Reddy et al. | |
| 2003/0109709 | A1 | 6/2003 | Reddy et al. | |
| 2003/0199707 | A1 | 10/2003 | Reddy et al. | |

FOREIGN PATENT DOCUMENTS

| | | |
|---|---|---|
| WO | WO 98/16517 | 0/1997 |
| WO | WO 92/05162 | 4/1992 |
| WO | WO 92/19604 | 11/1992 |

OTHER PUBLICATIONS

Yang, et al. 1998. J. Org. Chem. 63:2656-2660 "New Electrophilic Trifluoromethylating Agents".

Duan, et al. 1998. J. Org. Chem. 63:9486-9489 "A new and improved synthesis of trans-1, 2-Diiodalkenes and their sterospecific and highly regioselective trifluoromethylation".

Talley, et al. 2000. J. Med. Chem. 43:775-777 "4-[5-Methyl-3-phenylisoxazol-4-yl]-benzenesulfonamide, Valdecoxib: A potent and selective inhibitor of COX-2".

Talley, et al. 2000 J. Med. Chem. 43:1661-1663 "N-[[(5-Methyl-3-phenylisoxazol-4-yl)-phenyl] sulfonyl]propanamide, sodium salt, parecoxib sdium: A potent and selective inhibitor of COX-2 for parenteral administration".

Habeeb, et al. 2001. 44:2921-2927 "Design and synthesis of 4,5-Diphenyl-4-isoxazolines: novel inhibitors of cyclooxygenase-2 with analgesic and antiinflammatory activity".

(Continued)

*Primary Examiner*—Kamal A. Saeed
(74) *Attorney, Agent, or Firm*—Fox Rothschild, LLP (57) ABSTRACT

Provided are compounds, processes and synthetic intermediates useful for the preparation of compounds of the formula I and IX

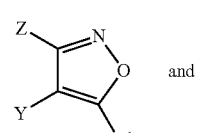

and

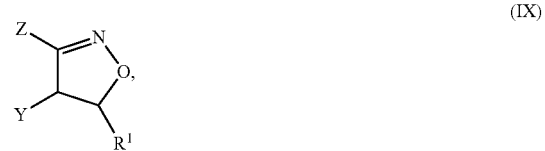

wherein $R^1$ is selected from the group consisting of hydrogen, trihalomethyl, $C_1$–$C_6$ alkyl and substituted or unsubstituted phenyl; Y is a group of the formula

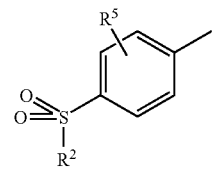

wherein $R^2$ is selected from the group consisting of $C_1$–$C_6$ alkyl, $C_1$–$C_6$ alkanoylamino and amino; and $R^5$ is selected from the group consisting of hydrogen, amino, halogen, hydroxyl, nitro, $C_1$–$C_6$ alkyl, $C_1$–$C_6$ alkoxy, carboxy, $C_1$–$C_6$ trihaloalkyl, cyano, phosphonato, and hydroxyalkyl; and Z is selected from the group consisting of substituted and unsubstituted aryl. Also provided are certain N-acylated analogs of compounds of the formula I and IX, and processes for their preparation.

22 Claims, 2 Drawing Sheets

OTHER PUBLICATIONS

Liu, et al. 2001. Tetrahedron Letters. 42:6147-6150 "One-pot synthesis of trans-B-alkylstyrenes".

Liu, et al. 2001. J. Org. Chem. 66:6021-6028 "Novel synthesis of alkenes via triethylborane-induced free-radical reactions of alkyl iodides and B-nitrostyrenes".

SciFinder Search.

Battaglia, et al. 1970. Tetrahedron Lett. 15:1221-4 Isoxazoles from nitrile oxides and arylacetylenes.

Battaglia, et al. 1970. J. Heterocyc. Chem. 7(3):721-4 "Soxazoles from nitrile oxides and acetylenes."

Abu-Orabi, et al. 1988. J. Chem. Eng. 33(4):540-1 "Cycloaddition reactions of 2,4,6-trimethoxybenzonitrile oxide with disubstituted acetylenes."

PROCESSES FOR THE PREPARATION OF SUBSTITUTED ISOXAZOLES AND 2-ISOXAZOLINES

This application claims the benefit of the priority of U.S. Provisional Patent Application No. 60/328,901, filed Oct. 12, 2001, and a division of U.S. patent application Ser No. 10/269,559, filed Oct. 11, 2002 now U.S. Pat. No. 6,809,204, the disclosure of which is hereby incorporated by reference as if fully set forth herein.

The present invention relates to substituted isoxazoles and 2-isoxazolines, and processes for their preparation. In addition the invention relates to compounds that serve as useful intermediates in the preparation of these heterocycles. Substituted isoxazoles are useful in the treatment of inflammation and inflammation-related disorders, including arthritis.

Selective inhibitors of cyclooxygenase-2 (COX-2) have demonstrated effective anti-inflammatory activity. Other antiinflammatory agents, e.g., NSAIDs, inhibit both the constitutive form of cyclooxygenase (COX-1), and the inducible form of the enzyme, COX-2.

COX-1 is a constitutive cyclooxygenase isoform and is mainly responsible for the synthesis of cytoprotective prostaglandins in the GI tract and the synthesis of thromboxane which triggers platelet aggregation in blood platelets. COX-2 is inducible and short-lived except in the case of certain tumors where it is constitutively activated. COX-2 expression is stimulated in response to endotoxins, cytokines, hormones, growth factors and mitogens. These observations suggest that COX-1 and COX-2 serve different physiological and pathophysiological functions. It has been suggested that COX-2 activity is mainly responsible for the pathological effects of prostaglandins where induction of the enzyme occurs in response to inflammatory agents, hormones, growth factors and cytokines. U.S. Pat. No. 5,604,253, incorporated herein by reference, for a discusses the advantages of selective COX-2 inhibition. Principally, a selective COX-2 inhibitor is expected to possess similar antiinflammatory, antipyretic and analgesic properties to conventional NSAIDs but with reduced potential for gastrointestinal toxicity, and a reduced potential for renal side effects.

A particularly effective structural class of selective COX-2 inhibitors are the 3,4-diaryl-substituted isoxazoles. For example, the compound, 4-[5-methyl-3-phenyl-isoxazol-1-yl]benzenesulfonamide (also known as Valdecoxib®) is useful for the treatment of a number of inflammation disorders, including osteoarthritis and rheumatoid arthritis. In addition, the sodium salt of N-[[(5-methyl-3-phenylisoxazol-4-yl)-phenyl]sulfonyl]propanamide (also known as Parecoxib®), a prodrug of Valdecoxib®, is particularly effective in parenteral compositions for acute pain management.

Valdecoxib®

Parecoxib sodium®

Talley et al. (U.S. Pat. No. 5,932,598 and *J. Med. Chem.* 2000, 43, 775–777) disclose the preparation of Valdecoxib® and related derivatives from deoxybenzoin. In the preparation, deoxybenzoin is treated with hydroxylamine, and the resulting oxime is deprotonated and condensed with an ester, e.g., ethyl acetate, to form an isoxazoline intermediate. The isoxazoline intermediate is converted Valdecoxib® by treatment with chlorosulphonic acid, followed by aqueous ammonia. Parecoxib sodium® can be prepared by acylation of Valdecoxib® with propionic anhydride (Talley et al., *J. Med. Chem.* 2000, 43, 1661–1663).

Also of interest for their COX-2 inhibitory activity and antiinflammatory activity are closely related analogs of Valdecoxib®, as well as processes for their preparation.

SUMMARY OF THE INVENTION

In one embodiment, the invention relates to a process for the preparation of a compound of the formula I wherein $R^1$ is selected from the group consisting of hydrogen, trihalomethyl, preferably trifluoromethyl; $C_1$–$C_6$ alkyl, preferably $C_1$–$C_3$ alkyl, most preferably methyl; and a group of the formula II wherein $R^3$ and $R^4$ are independently selected from the group consisting of hydrogen; amino; halogen; preferably chlorine, fluorine and bromine; hydroxyl; nitro; $C_1$–$C_6$ alkyl, preferably $C_1$–$C_3$ alkyl; $C_1$–$C_6$ alkoxy, preferably $C_1$–$C_3$ alkoxy; carboxy; $C_1$–$C_6$ trihaloalkyl, preferably trihalomethyl, most preferably trifluoromethyl; cyano; alkylsulfonyl; sulfamyl; phosphonato; and hydroxyalkyl, preferably $C_1$–$C_6$ hydroxyalkyl;

Y is a group of the formula wherein $R^2$ is selected from the group consisting of $C_1$–$C_6$ alkyl, preferably $C_1$–$C_3$ alkyl; $C_1$–$C_6$ alkanoylamino; and amino; and $R^5$ is selected from the group consisting of hydrogen; amino; halogen; preferably chlorine, fluorine and bromine; hydroxyl; nitro; $C_1$–$C_6$ alkyl, particularly $C_1$–$C_3$ alkyl; $C_1$–$C_6$ alkoxy, particularly $C_1$–$C_3$ alkoxy, preferably methoxy; carboxy; $C_1$–$C_6$ trihaloalkyl, preferably trihalomethyl, most preferably trifluoromethyl; cyano, phosphonato, and hydroxyalkyl, preferably $C_1$–$C_6$ hydroxyalkyl; and Z is selected from the group consisting of substituted and unsubstituted aryl.

The process has the step of contacting an oxime of the formula III (III)

with an oxidizing agent and reacting the resulting nitrile oxide with an alkyne of the formula IV (IV)

In another embodiment, the invention relates to a compound of the formula IX

(IX)

and pharmaceutically acceptable salts thereof, wherein $R^1$ is selected from the group consisting of hydrogen; trihalomethyl, preferably trifluoromethyl; $C_1$–$C_6$ alkyl, preferably $C_1$–$C_3$ alkyl, most preferably methyl; and a group of the formula II (II)

wherein $R^3$ and $R^4$ are independently selected from the group consisting of hydrogen; amino; halogen, preferably chlorine, fluorine and bromine; hydroxyl; nitro; $C_1$–$C_6$ alkyl, preferably $C_1$–$C_3$ alkyl; $C_1$–$C_6$ alkoxy, preferably $C_1$–$C_3$ alkoxy; carboxy; $C_1$–$C_6$ trihaloalkyl, preferably trihalomethyl, most preferably trifluoromethyl; cyano; alkylsulfonyl; sulfamyl; phosphonato; and hydroxyalkyl;

Y is a group of the formula wherein $R^2$ is selected from the group consisting of $C_1$–$C_6$ alkyl, preferably $C_1$–$C_3$ alkyl; $C_1$–$C_5$ alkanoylamino; and amino; and $R^5$ is selected from the group consisting of hydrogen; amino; halogen; preferably chlorine, fluorine and bromine; hydroxyl; nitro; $C_1$–$C_6$ alkyl, particularly $C_1$–$C_3$ alkyl; $C_1$–$C_6$ alkoxy, particularly $C_1$–$C_3$ alkoxy, preferably methoxy; carboxy; $C_1$–$C_6$ trihaloalkyl, preferably trihalomethyl, most preferably trifluoromethyl; cyano; phosphonato, and hydroxyalkyl, preferably $C_1$–$C_6$ hydroxyalkyl; and Z is selected from the group consisting of substituted and unsubstituted aryl.

In preferred embodiments of the compound of formula IX, $R^2$ is amino. In particularly preferred embodiments, $R^2$ is amino or propionylamino, $R^1$ is methyl, $R^5$ is hydrogen and Z is phenyl.

In other preferred embodiments of the compound of formula IX, $R^2$ is $C_1$–$C_6$ alkanoylamino, preferably n-propionylamino. In particularly preferred embodiments, $R^2$ is propionylamino, $R^1$ is methyl, $R^5$ is hydrogen and Z is phenyl.

The invention is also directed to isolated optical isomers of compounds according to formulas IX. By "isolated" means a compound which has been substantially purified from the corresponding optical isomer(s) of the same formula. The isomers can be purified by techniques that are well known in the art. For example, optical isomers can be separated by formation of diastereomeric addition salts with homochiral amines or acids. Alternatively, optical isomers can be separated by chiral chromatography on columns packed with chiral packing materials. Preferably, the isolated isomer is at least about 80%, more preferably, at least 90% pure, even more preferably at least 98% pure, most preferably at least about 99% pure, by weight. Preferably, the stereoisomer isolated is the one possessing the more potent antiinflammatory activity.

The invention is also directed to a pharmaceutical composition of one or more compounds of formula IX in combination with a pharmaceutically acceptable carrier.

According to another embodiment of the invention, a method for treating a cyclooxygenase-mediated disease is provided, that includes the step of administering an effective amount of a compound of the formula IX to an animal in need of such treatment. The terms "animal", "subject" and "patient" include human beings.

The compounds of the formula IX are prepared by a process that includes the step of contacting an oxime of the formula III (III)

with an oxidizing agent and reacting the resulting nitrile oxide with an alkene of the formula X (X)

wherein Y, Z and $R^1$ are as defined above.

In the processes and compounds of the invention, the aryl group Z includes phenyl and heteroaryl, which may be substituted or unsubstituted. By "substituted" is meant any level of substitution, although mono- di- and tri-substitution are preferred. The substituents are independently selected. The substituents are preferably selected from the group consisting of halogen, particularly chlorine, fluorine and bromine; hydroxyl; amino; nitro; $C_1$–$C_6$ alkyl, preferably $C_1$–$C_3$ alkyl, most preferably methyl; $C_1$–$C_6$ alkoxy, preferably $C_1$–$C_3$ alkoxy, most preferably methoxy; carboxy; $C_1$–$C_6$ trihaloalkyl, preferably trihalomethyl, most preferably trifluoromethyl; and cyano.

Although mono-, di- and tri-substitution is preferred, full substitution, particularly when the aryl group is phenyl, is possible.

According to certain embodiments of the processes, Z is substituted or unsubstituted heteroaryl. Such heteroaryl radicals include, for example, pyridyl, particularly 2-, 3- and 4-pyridyl; thienyl, particularly 2- and 3-thienyl; furyl, particularly 2- and 3-furyl; indolyl, particularly 3-, 4-, 5-, 6- and 7-indolyl; benzothienyl, particularly 3-, 4-, 5-, 6- and 7-benzothienyl; benzofuryl, particularly 3-, 4-, 5-, 6- and 7-benzofuryl; imidazolyl, particularly 2- and 5-imidazolyl; pyrazolyl, particularly 3- and 5-pyrazolyl; 2-thiazolyl; 2-benzothiazolyl; quinolinyl, particularly 2-, 3- and 4-quinolinyl; and 4-(2-benzyloxazolyl). In some preferred embodiments, Z is 3-indolyl. Representative preferred substituted heteroaryl groups include 6-methyl-2-pyridyl, 5-halo-2-thienyl, 5-methyl-2-thienyl, 5-halo-2-furyl, 5-halo-3-furyl, 2,5-dimethyl-3-thienyl and 2,5-dimethyl-3-furyl.

In other embodiments of the processes, Z is selected from the group consisting of unsubstituted phenyl, mono-, di- and trisubstituted phenyl. Preferred radicals wherein Z is substituted phenyl include, for example, one or more of amino, halogen, hydroxyl, nitro, $C_1$–$C_6$ alkyl, $C_1$–$C_6$ alkoxy, carboxy, $C_1$–$C_6$ trihaloalkyl and cyano.

In preferred embodiments of the processes, $R^1$ is methyl, $R^2$ is amino or n-propionylamino, $R^5$ is hydrogen and Z is phenyl.

In another aspect, the processes of the invention include preparations of the alkyne of the formula IV (IV)

wherein $R^1$ is hydrogen, trihalomethyl, $C_1$–$C_6$ alkyl and a group of the formula II.

In other embodiments, the processes of the invention include preparations of the alkene of the formula X (X)

wherein $R^1$ is hydrogen, trihalomethyl, $C_1$–$C_6$ alkyl and a group of the formula II.

In other aspects, the invention relates to processes for preparing a compound of the formula Ib (Ib)

or a compound of the formula IXb

(IXb)

wherein $R^1$ and $R^5$ are as described above and $R^6$ is $C_1$–$C_5$ alkyl, preferably $C_1$–$C_3$, more preferably ethyl; and their corresponding alkali metal salts (formed from the deprotonation of the alkanamide moieties).

In another aspect, the invention relates to a compound of the formula wherein $R^1$ is hydrogen, trihalomethyl, $C_1$ to $C_6$ lower alkyl or a group of the formula II (II)

wherein
$R^3$ and $R^4$ are independently selected from the group consisting of hydrogen, amino, halogen, hydroxyl, nitro, $C_1$–$C_6$ alkyl, $C_1$–$C_6$ alkoxy, carboxy, $C_1$–$C_6$ trihaloalkyl, cyano, alkylsulfonyl, sulfamyl, phosphonato and hydroxyalkyl;
$R^2$ is selected from the group consisting of amino, $C_1$–$C_6$ alkanoylamino or $C_1$–$C_6$ lower alkyl; and
$R^5$ is selected from the group consisting of hydrogen, amino, halogen, hydroxyl, nitro, $C_1$–$C_6$ alkyl, $C_1$–$C_6$ alkoxy, carboxy, $C_1$–$C_6$ trihaloalkyl, cyano, phosphonato, and hydroxyalkyl.

DETAILED DESCRIPTION OF THE INVENTION

Figure 1:
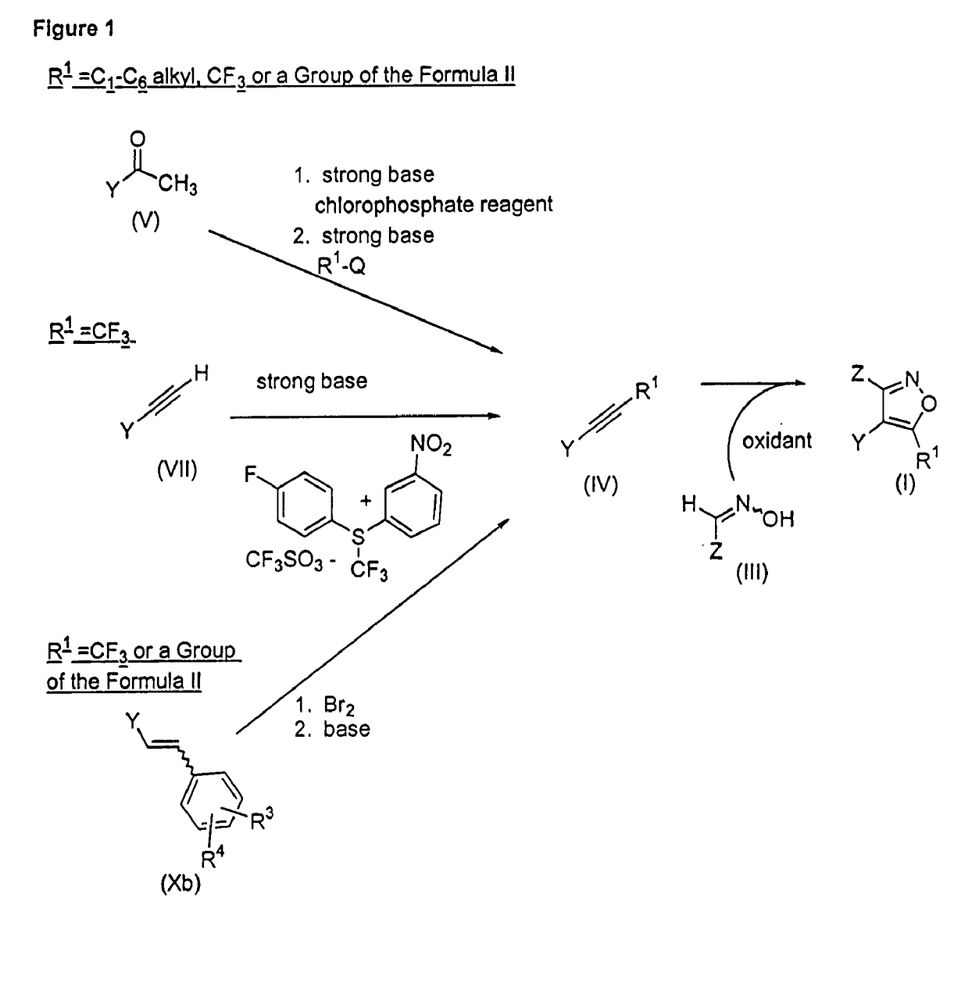
FIG. 1 depicts some embodiments of the process for the preparation of the compound of the formula I.
Figure 2:
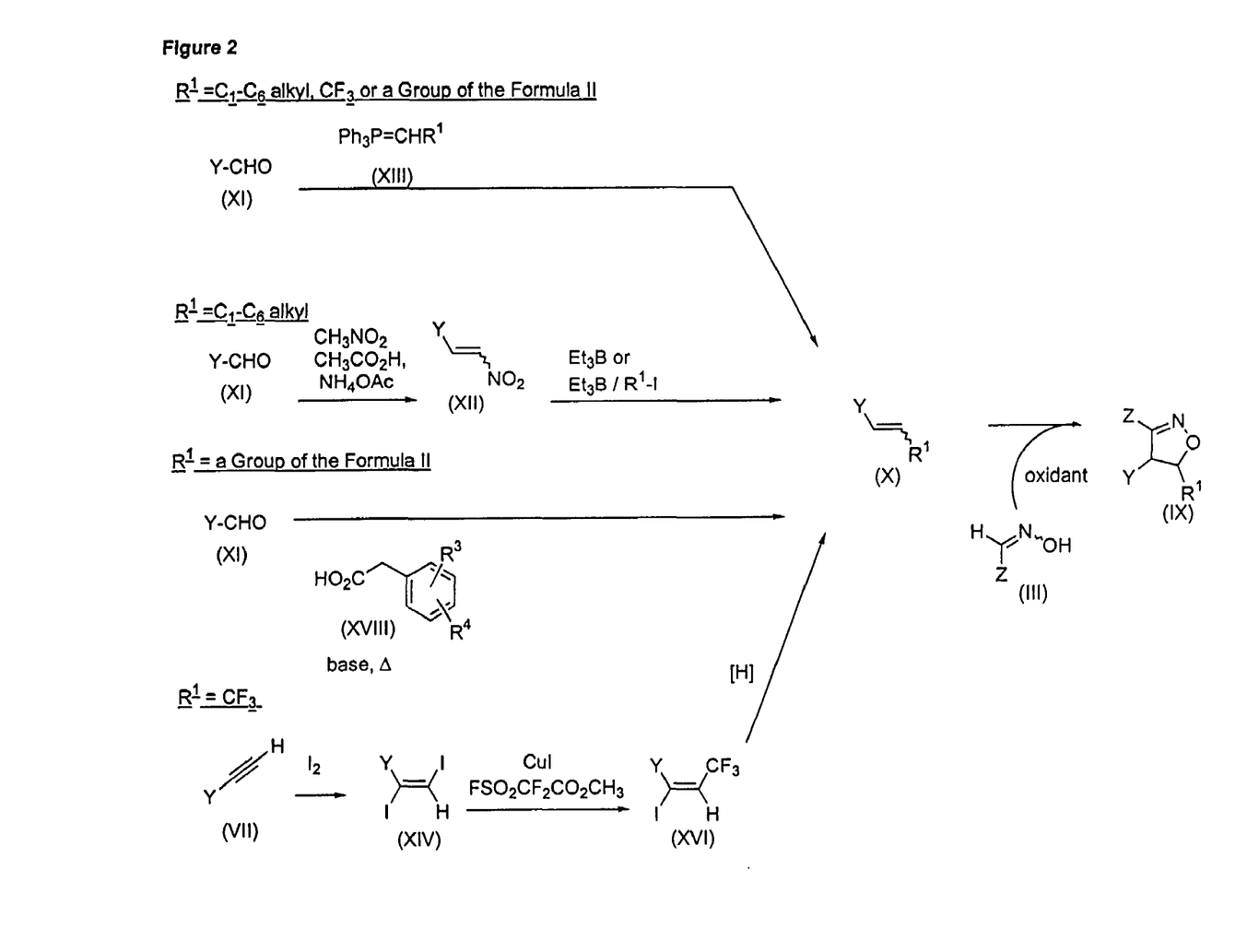
FIG. 2 depicts some embodiments of the process for the preparation of the compound of the formula IX.

The following terms shall have, for the purposes of this application, the respective meanings set forth below.
"Alkanoylamino" includes linear and branched alkanoylamino groups, e.g., acetamido-, propionylamido-, pivaloylamido-, and the like.
"Alkoxy" includes linear and branched alkoxy groups, e.g., methoxy, ethoxy, t-butyloxy, and the like.
"Alkyl" includes linear and branched alkyl groups, e.g., methyl, ethyl, t-butyl, and the like.
"Aryl" alone or in combination, includes carbocyclic aromatic systems or a heterocyclic aromatic systems (also known as heteroaryl). The systems may contain one, two or three rings wherein such ring may be attached together in a pendent manner or may be fused.
"Chlorophosphate reagent" includes dialkyl chlorophosphates (e.g., dimethyl and diethyl chlorophosphates) and diaryl chlorophosphates (e.g., diphenyl chlorophosphate).
"Effective amount" will be recognized by clinicians but includes an amount effective to reduce, ameliorate or eliminate one or more symptoms with any disorder characterized by undesirable prostaglandin production resulting from cyclooxygenase activity, particularly COX-2 activity ("cyclooxygenase-mediated disorder").
"Inert organic solvent" means any organic solvent or combination of solvents that is unreactive in the reaction being conducted, and is a solvent for the reactants. Examples of such solvents used in the various reactions of this invention are identified in the discussion of the reaction schemes and in the examples.
"Strong base" means a non aqueous base such as sodium-, potassium-, lithium hexamethyldisilazide, lithium diisopropyl amide, and the like.

"Trialkylamine" includes triethylamine, N,N-dimethylethylamine, N,N-diisopropylethylamine, and the like.

In accordance with the present invention, novel processes and synthetic intermediates for the preparation of substituted isoxazoles of the formula I (I)

are provided. In addition the invention provides substituted 2-isoxazolines of the formula IX (IX)

and processes for their preparation. The 2-isoxazoline compounds of the formula IX are structurally similar to the isoxazole compounds of the formula I as the isoxazoline compounds are 4,5-dihydro analogs of the isoxazole compounds. In addition to their structural similarity, their synthetic preparations share analogous reaction pathways and certain common synthetic intermediates. The processes of the invention have been developed from readily available and inexpensive starting materials. In addition, the processes provide high yields of substituted isoxazoles and 2-isoxazolines.

Substituted Isoxazoles (Compound of the Formula I)

In one embodiment of the invention, the compound of the formula I (I)

is prepared by a [3+2] cycloaddition of an alkyne of the formula IV (IV)

with a nitrile oxide, that is formed by oxidation of an oxime of the formula III wherein $R^1$, Y and Z are as described above in the summary.

The nitrile oxide is generally generated in situ from the oxime of the formula III by oxidation with a suitable oxidizing agent, e.g. N-chloro-p-toluenesulfonamide, sodium salt; alkaline sodium hypochlorite; chlorine; N-bromosuccinimide; lead tetraacetate, in an alcohol solvent, e.g., methanol. The nitrile oxide (isolated after water workup) is added directly to the alkyne of the formula IV in an alcohol solvent, e.g., ethanol, and the reaction mixture is heated to about 70° C. to about 80° C. for about 30 minutes to about 6 h, preferably about 3 h to give the desired isoxazole. Preferably, equimolar amounts of the nitrile oxide and the alkyne of the formula IV are used. After water workup the organic layer is concentrated to isolate the crude substituted isoxazole of the formula I. The compound of the formula I can be further purified by recrystallization in suitable solvents such as ethanol.

In certain embodiments, particularly wherein $R^1$ is a group of the formula II (phenyl or substituted phenyl) in the alkyne of the formula III, the cycloaddition step may result in mixtures of regioisomers. As will be apparent to those of ordinary skill in the art, these mixture can be separated by well-known separation techniques, e.g., chromatography, recrystallization, and the like, to obtain the desired regioisomer.

Various acid addition salts of the compound of the formula I can be prepared by treatment with an organic or inorganic acid. Preferably, the acid addition salts formed are pharmaceutically acceptable salts, such as those described in U.S. Pat. No. 5,563,165, the disclosure of which is herein incorporated by reference. Suitable base addition salts of the compound of formula I, wherein the phenyl group at the 5-position of the pyrazole ring incorporates a carboxy or hydroxyl substituent. Base addition salts include metallic addition salts, e.g., sodium, potassium, and organic base addition salts, e.g, organic amines. Other pharmaceutically acceptable acid addition salts are detailed in U.S. Pat. No. 5,563,165.

Preparation of Alkynes of the Formula IV, wherein $R^1$ is $C_1$–$C_6$ Alkyl or Hydrogen In embodiments of the invention where $R^1$ is $C_1$–$C_6$ alkyl, the alkyne of the formula IV can be obtained by deprotonation of a methyl ketone of the formula V wherein Y is as described above, with a strong base, e.g., lithium diisopropylamide, in an anhydrous ethereal solvent, e.g. tetrahydrofuran, at a temperature below 5° C., preferably about 0° C. Typically, a slight molar excess of the strong base is used in the deprotonation step, preferably about 5 to 10% molar excess. The deprotonation is carried out for a period of about 15 to 45 minutes, preferably about 30 minutes. A chlorophosphate reagent, preferably diethyl chlorophosphate, is subsequently added to the reaction mixture to form a phosphonate intermediate that is typically not isolated. The solution containing the phosphonate intermediate is then treated with at least two molar equivalents of strong base, e.g., lithium diisopropylamide, at a temperature of about −10° C. to about 10° C., preferably about 0° C. An alkylating agent of the formula VI

$$R^1\text{-}Q \tag{VI}$$

wherein Q is a leaving group, e.g., halide, mesylate, tosylate and the like, can be added to the reaction mixture, and the resulting mixture is heated to provide the alkyne of formula IV. A cosolvent such as hexamethylphosphoramide (HMPA) can be added to the reaction mixture to enhance the efficiency of the alkyne formation. The alkyne of the formula IV is typically used directly in the [3+2] cycloaddition step without isolation. In preferred embodiments, wherein $R^1$ is methyl, methyl iodide is a preferred alkylating agent.

In embodiments of the process wherein Y is phenyl substituted by a group of the formula —$SO_2R^2$, wherein $R^2$ is $C_1$–$C_6$ alkyl, the methyl ketones of the formula V can be prepared by methods well known to those of ordinary skill in the art. For example, acetophenone can be reacted with alkyl sulfonyl halides e.g., $CH_3SO_2F$, in Friedel-Craft type reactions. Alternatively, methyl ketones containing alkyl sulfonyl substituents can be prepared by oxidation of phenyl alkyl thioethers.

In other preferred embodiments of the process, wherein Y is phenyl substituted by a group of the formula —$SO_2R^2$, wherein $R^2$ is amino, the methyl ketones of the formula V can be prepared by treating the acetophenone of the formula XV, with ammonium hydroxide at room temperature as depicted in the preparation of 4-sulfamylacetophenone (Va) in Scheme 1. The sulfonamido moiety can be acylated with an acylating agent of the formula XIX, wherein $R^6$ is $C_1$–$C_5$ alkyl, preferably $C_1$–$C_3$ alkyl, in the presence of a trialkylamine base, e.g. triethylamine, to give the compound of the formula XXI, wherein $R^6$ is $C_1$–$C_5$ alkyl.

Scheme 1

-continued

Va (XIX)

XXI

Preparation of Alkynes of the Formula IV wherein $R^1$ is Trifluoromethyl

The alkyne of the formula IV wherein $R^1$ is trifluoromethyl can be prepared from a substituted phenyl acetylene of the formula VII (VII)

wherein Y is as described above, by forming the corresponding acetylide using a strong base, e.g., n-butyl lithium, in an ethereal solvent, e.g., tetrahydrofuran, and then alkylating the acetylide with a trifluoromethyl alkylating reagent such as S-(trifluoromethyl)phenyl-4-fluorophenyl-3-nitrophenyl-sulfonium triflate (prepared as described in Yang et. al. *J. Org. Chem.* 1998, 63, 2656) to give the alkyne of the formula IVb (IVb)

The reaction is typically conducted at temperatures of –80° C. to 25° C., preferably about –78° C. for about 2 to about 5 hours.

Preparation of Alkynes of the Formula IV wherein $R^1$ is a Group of the Formula II The alkyne of the formula IV, wherein $R^1$ is a group of the formula II (II)

wherein $R^3$ and $R^4$ are as described above, can be obtained by the method depicted in Scheme 2. An alkene of the formula Xb (obtained by the method described below) is first treated with bromine in a suitable inert organic solvent, e.g., chloroform, at room temperature for a sufficient amount of time to form a dibromo intermediate at about room temperature. The dibromo intermediate is subsequently treated with a base, such as an alkali metal hydroxide, e.g., potassium, sodium, or lithium hydroxide, in an alcohol solvent, e.g., ethanol, at temperatures of about 60 to about 100° C. to effect elimination of HBr and provide the alkyne of formula IVa. The alkyne of the formula IVa can be further purified by, for example, by recrystallization from suitable solvents, e.g., alcohols, when the compound is a solid. Alternatively, the compound of the formula IVa can be purified by techniques such as chromatography or distillation (in the case of liquids).

In an alternative procedure, the alkyne of the formula IV, wherein $R^1$ is a group of the formula II can be obtained by treating a substituted phenyl acetylene of the formula VII (VII)

wherein Y is as described above, with a copper (II) salt, and reacting the resulting copper acetylide with a compound of the formula VIII (VIII)

wherein Q' is chloro, bromo or iodo, preferably iodo. Typically, the corresponding copper acetylide of the substituted phenyl acetylene of the formula VII is generated by reaction with the copper II salt, e.g., copper sulfate in the presence of aqueous ammonia and hydroxylamine.

Substituted 2-Isoxazolines (Compound of the Formula IX)

The invention also relates to compounds of the formula IX (IX)

wherein $R^1$, Y and Z are as described above in the summary section.

The compounds of the formula IX preferably are characterized by a selectivity ratio for COX-2 inhibition over cyclooxygenase-1 (COX-1) inhibition of at least about 50, more preferably at least about 100. COX inhibition may be determined in vitro by enzyme assays well-known to those skilled in the art, such as the enzyme assay method described later herein.

The compounds of the present invention may take the form of pharmaceutically acceptable salts. The term "pharmaceutically acceptable salts", embraces salts commonly used to form alkali metal salts and to form addition salts of free acids or free bases. Where reference is made to "compound of formula IX (including IXb)", it is understood that pharmaceutically acceptable salts are also included. The nature of the salt is not critical, provided that it is pharmaceutically-acceptable. Suitable pharmaceutically acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, galactaric and galacturonic acid. Suitable pharmaceutically acceptable base addition salts of compounds of formula IX (including IXb) include metallic salts made from calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts can be prepared by conventional means from the corresponding compound of formula IX by reacting, for example, the appropriate acid or base with the compound of formula IX.

The compounds of the formula IX may be administered in the form of a pharmaceutical composition, in combination with a pharmaceutically acceptable carrier. The active ingredient in such formulations can comprise from 0.1 to 99.99 weight percent. By "pharmaceutically acceptable carrier" is meant any carrier, diluent or excipient which is compatible with the other ingredients of the formulation and is not deleterious to the recipient.

The compounds of the formula IX may be administered to individuals (animals, most particularly mammals including humans) afflicted with any disorder characterized by undesirable prostaglandin production resulting from cyclooxygenase activity, particularly COX-2 activity ("cyclooxygenase-mediated disorder"). In particular, the compounds of the formula IX are believed useful in treating inflammation and inflammation-related disorders, by administering to a subject having or susceptible to such inflammation or inflammation-related disorder an effective amount of a compound according to formula IX. Inflammation is associated with a variety of disease conditions. For a list of such disease conditions treatable by cyclooxygenase inhibitors, and COX-2 inhibitors in particular, see U.S. Pat. Nos. 5,604,253 and 5,908,852, the entire disclosures of which are incorporated herein by reference. Such conditions include, for example, arthritis, including but not limited to rheumatoid arthritis, spondyloarthropathies, gouty arthritis, osteoarthritis, systemic lupus erythematosus and juvenile arthritis. Such conditions further include rheumatic fever, symptoms associated with influenza or other viral infections, common cold, lower back and neck pain, dysmenorrhea, headache, toothache, sprains and strains, myositis, neuralgia, synovitis, gout and ankylosing spondylitis, bursitis, and following surgical and dental procedures. The compounds of the formula IX are believed useful as analgesics for treating or alleviating all forms of pain. The compounds are believed useful in the treatment of other disorders including asthma, bronchitis, tendinitis, bursitis; skin related conditions such as psoriasis, eczema, burns and dermatitis; gastrointestinal conditions such as inflammatory bowel disease, Crohn's disease, gastritis, irritable bowel syndrome and ulcerative colitis and for the prevention of colorectal cancer; the treatment of inflammation in such diseases as vascular diseases, migraine headaches, periarteritis nodosa, thyroiditis, aplastic anemia, Hodgkin's disease, scleroderma, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds of the formula IX are believed useful as antipyretics for the treatment of fever.

In addition, compounds of the formula IX may be useful in the treatment of Alzheimer's disease and mild cognitive impairment.

In addition, compounds of the formula IX may inhibit cellular neoplastic transformations and metastatic tumor growth and hence can be used in the treatment of cancer. In particular, the present invention provides a method for treating or preventing a neoplasia that produces a prostaglandin in a subject in need of such treatment or prevention, the method includes treating the subject with a therapeutically effective amount of a compound of formula IX. The term "neoplasia" includes neoplasias that produce prostaglandins or express a cyclooxygenase, including both benign and cancerous tumors, growths and polyps. Neoplasias believed treatable with cyclooxygenase inhibitors are discussed in U.S. Pat. No. 5,972,986, the entire disclosure of which is incorporated herein by reference. The compounds may be used to inhibit the growth of an established neoplasm, i.e., to induce regression, or to prevent or delay the onset of the neoplasm.

According to U.S. Pat. No. 5,972,986, neoplasias that produce prostaglandins, and which are therefore believed treatable with the compounds of the invention, include brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreatic cancer, ovarian cancer, cervical cancer, lung cancer, breast cancer and skin cancer, such as squamous cell and basal cell cancers, prostate cancer, renal cell carcinoma, and other known cancers that effect epithelial cells throughout the body.

The compounds of the formula IX may also be useful in the treatment of angiogenesis-mediated disorders. Thus, a method for treating, inhibiting or delaying the onset of an angiogenesis-mediated disorder in a subject is provided comprising administering to a subject in need of such treatment an effective amount of a compound according to the present invention. Angiogenesis-mediated disorders which may be treatable with cyclooxygenase inhibitors are discussed in U.S. Pat. No. 6,025,353, the entire disclosure of which is incorporated herein by reference. According to U.S. Pat. No. 6,025,353, such disorders include, for example, metastasis, corneal graft rejection, ocular neovascularization, retinal neovascularization, diabetic retinopathy, retrolental fibroplasia, neovascular glaucoma, gastric ulcer, infantile hemaginomas, angiofibroma of the nasopharynx, avascular necrosis of bone, and endometriosis.

The compounds may be administered by any route, including oral and parenteral administration. Parenteral administration includes, for example, intravenous, intramuscular, intraarterial, intraperitoneal, intranasal, rectal, or subcutaneous administration. The active agent is preferably administered with a pharmaceutically acceptable carrier selected on the basis of the selected route of administration and standard pharmaceutical practice.

The active agent may be formulated into dosage forms according to standard practices in the field of pharmaceutical preparations. See Alphonso Gennaro, ed., *Remington's Pharmaceutical Sciences*, 18th *Ed.*, (1990) Mack Publishing Co., Easton, Pa. Suitable dosage forms may include, for example, tablets, capsules, solutions, parenteral solutions, troches, suppositories, or suspensions.

For parenteral administration, the active agent may be mixed with a suitable carrier or diluent such as water, an oil, saline solution, aqueous dextrose (glucose) and related sugar solutions, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol.

For oral administration, the active agent may be combined with one or more solid inactive ingredients for the preparation of tablets, capsules, or other suitable oral dosage forms. For example, the active agent may be combined with carboxymethylcellulose calcium, magnesium stearate, mannitol and starch, and then formed into tablets by conventional tableting methods.

The specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.01 to about 150 mg/kg/day may be utilized. Higher or lower doses are also contemplated.

The compounds of the formula IX contain two chiral carbon atoms at positions 4 and 5 of the isoxazoline nucleus. The present invention is meant to comprehend all stereoisomers of the compound of the formula IX including isolated optical isomers, isolated diastereoisomers and mixtures thereof (including pharmaceutically acceptable salts thereof). In addition, other chiral carbon atoms may also be present in the compound.

Diastereoisomers can be isolated by well-known techniques including chromatography and recrystallization techniques. Isolated optical isomers may be purified from racemic mixtures by well-known chiral separation techniques. According to one such method, a racemic mixture of a compound having the structure of formula IX or chiral intermediate thereof, is separated into 99% wt. % pure optical isomers by HPLC using a suitable chiral column, such as a column containing a packing of chiral phase material bonded to silica gel.

The compound of the formula IX wherein $R^1$, Y and Z are as described above in the summary section, can be obtained by a [3+2] cycloaddition of a nitrile oxide obtained from the oxidation of the oxime of the formula III and an alkene of the formula X

The nitrile oxide is generated from the oxime as described above in the synthesis of the isoxazole compound of the formula I. The nitrile oxide is typically mixed with the alkene of the formula X in an alcohol solvent, e.g., ethanol, and the resulting mixture is heated to about 50° C. to about 100° C. for about 30 minutes to about 6 hours, preferably about 3 hours to give the desired substituted-2-isoxazoline. Preferably, equimolar amounts of the nitrile oxide and the alkene of the formula X are used. After water workup, the organic layer is concentrated to isolate the compound of the formula IX. The compound of the formula IX can be further purified by recrystallization in suitable solvents such as methanol.

In certain embodiments, particularly wherein $R^1$ is a group of the formula II (substituted or unsubstituted phenyl) in the alkene of the formula X, the cycloaddition step may result in mixtures of regioisomers. As will be apparent to those of ordinary skill in the art, these mixtures can be separated by well-known separation techniques, e.g, chromatography, recrystallization, and the like, to obtain the desired regioisomer.

Various acid addition salts of the compound of the formula IX can be prepared by treatment with an organic or inorganic acid. Preferably, the acid addition salts formed are pharmaceutically acceptable salts, such as those described in U.S. Pat. No. 5,563,165, the disclosure of which is herein incorporated by reference. Suitable base addition salts of the compound of formula I, wherein the phenyl group at the 5-position of the pyrazole ring incorporates a carboxy or hydroxyl substituent. Base addition salts include metallic addition salts, e.g, sodium, potassium, and organic base addition salts, e.g, organic amines. Other pharmaceutically acceptable acid addition salts are detailed in U.S. Pat. No. 5,563,165.

Preparation of Alkenes of the Formula X (General Methods)

The alkene of the formula X (X)

wherein $R^1$ is hydrogen, $C_1$–$C_6$ alkyl, trihalomethyl or a group of the formula II can be prepared by a number of processes known in the art. For example, a Wittig reaction can be conducted with a substituted phenyl aldehyde of the formula XI

Y—CHO      (XI), wherein Y is as described above, and a compound of the formula XIII Ph$_3$P=CHR$^1$      (XIII)

to give the alkene of the formula X. The compound of the formula XIII can be generated from the corresponding phosphonium salt Ph$_3$P—CH$_2$R$^1$+I— (or Br—)

by reaction with a strong base, e.g., n-butyllithium, in a suitable organic solvent, e.g., diethyl ether. The phosphonium salts, in turn, are either readily commercially available (e.g., Aldrich Chemical Co., Milwaukee, Wis.), or can be generated from the corresponding alkyl iodides or bromides by reaction with triphenylphosphine.

Preparation of Alkenes of the Formula X (wherein $R^1$ is $C_1$–$C_6$ alkyl)

In addition to Wittig-type condensations, additional procedures are also useful for the preparation of certain alkenes of the formula X, wherein $R^1$ is $C_1$–$C_6$ alkyl. For example, a Knoevenagel-type condensation of an aldehyde of the formula XI

Y—CHO      (XI)

with nitromethane yields a nitroalkene of the formula XII (XII)

(as described in Liu et al. (*Tetrahedron Lett.* 2001, 42, 6147–6150). Typically, the condensation is conducted in acetic acid with added ammonium acetate at between about 75–118° C. from about 3 hours to about 24 hours. The resulting nitroalkene is then treated with at least 3 molar equivalents of triethylborane (preferably about 4 equivalents) to give the alkene of the formula X wherein $R^1$ is ethyl. To prepare alkenes of the formula X, wherein $R^1$ is other than ethyl, the corresponding alkyl iodide (i.e., $R^1$ -I, 6–20 equivalents) can be added to the reaction mixture in addition to triethylborane. The reaction of the nitroalkene with triethylborane or triethylborane/alkyl iodide is conveniently conducted, for example, as a one-pot process by addition of diethyl ether and water to the Knoevenagel condensation reaction mixture. Alternatively, the intermediate nitroalkene can be isolated, and then subjected to the alkylation procedure in an ethereal solvent, e.g. tetrahydrofuran, at about room temperature (Liu et al. *J. Org. Chem.* 2001, 42, 6147–6150).

Preparation of Alkenes of the Formula X (wherein $R^1$ is a Group of the Formula II)

In another embodiment, a procedure for preparing an alkene of the formula X, wherein $R^1$ is a group of the formula II (II)

is provided. In the procedure a substituted phenyl aldehyde of the formula XI

Y—CHO      (XI), wherein Y is as described above, is condensed with a substituted or unsubstituted phenyl acetic acid of the formula XVII (XVII)

to give an alkene of the formula Xb (Xb)

In one typical procedure, the condensation reaction is conducted using a base, e.g., piperidine, without added solvent. Alternatively, the condensation can be conducted in acetic anhydride using triethylamine. The reaction temperatures for the condensations are about 120° C. to about 140° C. from about 8 to about 12 hours.

Preparation of Alkenes of the Formula X (wherein $R^1$ is Trifluoromethyl)

Another procedure provides a method for preparing an alkene of the formula X, wherein $R^1$ is trifluoromethyl. In this procedure, an alkyne of the formula VII (VII)

is treated with iodine (about 1 to 1.8 equivalents) to form a diiodo alkene of the formula (XIV)

The diiodo compound of the formula XIV is then reacted with a slight molar excess of a reagent of the formula

FSO$_2$CF$_2$CO$_2$CH$_3$ in the presence of a catalytic amount of copper iodide in a suitable organic solvent, e.g., dimethylformamide, at 60 to about 100° C., preferably about 75 to 80° C. to give an iodo-trifluoromethyl substituted alkene intermediate XVI (XVI)

The trifluoromethylating reagent can be prepared according to procedures described in Wiamers et al. *J. Am. Chem. Soc.* 1986, 108, 832. The intermediate XVI can then be reduced using, for example, about 3 to about 4 equivalents of zinc, a catalytic amount of silver acetate and acetic acid in dimethylformamide at 15 to about 35° C. for about 1 to about 24 hours. After water workup, the alkene of the formula Xa (Xa)

is isolated, for example, by distillation or chromatography. This procedure is exemplified in Duan et al., *J. Org. Chem.* 1998, 63, 9486–9489.

Alternatively, an alkene of the formula Xa can be obtained through controlled catalytic hydrogenation of the alkyne of the formula IVb (prepared as described above)

(IVb)

using, for example, a selective hydrogenation catalyst, e.g., Lindlar's catalyst, a nickel-boride catalyst, to give the alkene in a suitable inert organic solvent, e.g, ethanol.

Preparation of N-[[5-Substituted-3-phenylisoxal-4-yl)phenyl]sulfonyl]alkanamide and N-[[5-Substituted-3-phenyl-2-isoxalin-4-yl)phenyl]sulfonyl]alkanamides and their Salts (Compounds of the Formula Ib, Ib', IXb and IXb'.)

In another aspect the invention relates to a method of preparing a compound of the formula Ib (Ib)

or (IXb)

wherein R$^1$ and R$^5$ are as described above and R$^6$ is C$_1$–C$_5$ alkyl, and their corresponding base addition salts (formed from the deprotonation of the alkanamide moieties). The process for preparing for the compounds includes the step of preparing the compounds of the formulas Ia and IXa using the [3+2] cycloaddition process described above for the preparation of the compounds of the formula I and IX. The preparation of the isoxazole compound of the formula Ib and its corresponding base addition salt is shown in Scheme 3. Preferred base addition salts include alkali metal salts (wherein M+ is an alkali metal cation selected from sodium, potassium and lithium, preferably sodium in Scheme 3)

Scheme 3

After the cycloaddition step, the sulfonamide moiety of the compound of the formula Ia is acylated with an acylating agent of the formula XIX, wherein $R^6$ is $C_1$–$C_5$ alkyl, preferably $C_1$–$C_3$ alkyl, in the presence of a trialkylamine base, e.g. triethylamine, to give the compound of the formula Ib. It will be apparent to those of skill in the art that alternative acylating reagents can be used for the acylation including acid chlorides, activated esters, and the like. The corresponding alkali metal salt Ib' can be prepared by treatment of the compound of the formula Ib with an alkali metal base, e.g., an alkali metal hydroxide of the formula

M+OH—, wherein M+ is an alkali metal cation, preferably sodium cation. Typically the base treatment is performed using aqueous hydroxide solution.

Alternatively, the compound of the formula Ib can be prepared by preparing an alkyne of the formula IVd, having a sulfonamido moiety already in place, and treating the alkyne with a nitrile oxide in a [3+2] cycloaddition as described above.

The isoxazoline compound of the formula IXb and its corresponding basic addition salt can be formed using an analogous synthetic route as depicted in Scheme 4.

Scheme 4

Alternatively, the compound of the formula IXb can be prepared by preparing an alkene of the formula Xd, (Xd)

having a sulfonamido moiety already in place, and treating the alkene with a nitrile oxide in a [3+2] cycloaddition as described above.

In embodiments of the above processes wherein the substituted or unsubstituted phenyl group Y, the aryl group Z, or a group of the formula II (II)

bear substituents such as hydroxyl or carboxy that may interfere or decrease the yield of certain synthetic steps, suitable protecting groups for these substituents that are well known in the art, can be used. The protecting groups can be then removed at appropriate points in the synthetic sequence by known methods. Thus, for example, a hydroxyl moiety can be protected as a methyl or silyl ether. Similarly, a carboxy moiety can be protected as an ester if necessary, which can be hydrolyzed in a later synthetic step.

The following examples further illustrate the present invention, but of course, should not be construed as in any way limiting its scope.

EXAMPLE 1

Preparation of 3-(4-Chlorophenyl)-4-Phenyl Isoxazole (Compound of the Formula I wherein $R^1$=H, Y=4-phenyl and Z=4-chlorophenyl).

A solution of phenylacetylene (10 mmol), 4-chlorobenzaldoxime (10 mmol) and chloramine-T (10 mmol, N-chloro-p-toluenesulfoneamide, sodium salt) were dissolved in methanol (40 mL) and refluxed for 6 h. The contents of the flask were cooled and the precipitated material, which was a mixture of isoxazole and 4-toluenesulfonamide, was filtered and washed with water. The solid material on boiling in hot water kept the sulfonamide in solution while precipitating the isoxazole. The precipitated isoxazole was filtered and recrystallized from ethanol, yield (82%), m.p.: 178–180° C.; $^1$H NMR (DMSO-$d_6$) 6.75(s, 1H), 7.49–7.55(m, 5H), 7.77–7.82 (m, 4H).

EXAMPLE 2

Preparation of 4-[5-methyl-3-phenyl-isoxazol-1-yl] benzenesulfonamide (Compound of the Formula I wherein $R^1$=$CH_3$, Y=4-sulfamylphenyl and Z=phenyl)

Preparation of 4-sulfamyl acetophenone (Va):

To a solution of 4-acetylbenzene sulfonyl chloride (XV, 10 mmol) in ether (120 mL), ammonium hydroxide (4 mL) is added. After stirring at room temperature for 5 h, the solvent is removed, and the residue is stirred with 3 N HCl (100 mL) for 1 h and filtered. The solid obtained is washed with water, ether, and then dried under reduced pressure. The 4-sulfamyl acetophenone obtained is used in the next step without further purification.

Preparation of 1-(4-sulfamylphenyl)-1-Propyne (Alkyne of the Formula IV wherein Y is 4-sulfamylphenyl and $R^1$ is methyl, $R^2$=$NH_2$)

A solution of lithium diisopropylamide (5.25 mmol) in THF is charged to a dry two-necked flask flushed with nitrogen maintained at 0° C. To this solution, 4-sulfamylacetophenone (Va, 5 mmol) is added dropwise to the stirred solution with constant bubbling of the solution with dry nitrogen. The reaction mixture is stirred for 30 min at 0° C., followed by the addition of diethyl chlorophosphate (5.75 mmol).

A cooled solution of lithium diisopropylamide (12.5 mmol) is added to the stirred reaction mixture via syringe. To this reaction mixture 3 mL of hexamethylphosphoramide (HMPA) is added, and the reaction mixture is warmed to 5° C. followed by the addition of 2.5 mL (37.5 mmol) of iodomethane. At this point, the nitrogen inlet tube is replaced with a reflux condenser. The reaction mixture is refluxed for 1 h, followed by the addition of 10 mL of saturated ammonium chloride solution. After 5 minutes of stirring, 20 mL of ether is added. The mixture is shaken, and the ether layer is separated and evaporated to give 1-(4-sulfamylphenyl)-1-propyne.

Preparation of 4-[5-methyl-3-phenyl-isoxazol-1-yl]benzenesulfonamide:

A solution of benzaldehyde oxime (5 mmol) in methanol (15 mL) is heated to 30–40° C. Chloramine-T (5 mmol) is then added and the contents are heated to reflux. The solvent is removed in vacuo and the residue obtained is extracted with dichloromethane (100 mL), washed with 1 M NaOH, brine and then dried. Removal of the dichloromethane under reduced pressure yields the nitrile oxide. The nitrile oxide (5 mmol) is added to 1-(4-sulfamylphenyl)-1-propyne (5 mmol) in ethanol (50 mL) and the resulting mixture is refluxed for 3 h. The cooled reaction mixture is filtered, washed with brine and water. Concentration under reduced pressure gives 4-[5-methyl-3-phenyl-isoxazol-1-yl]benzenesulfonamide.

EXAMPLE 3

Preparation of β-Trifluoromethyl-phenylacetylene (Alkyne of the Formula IV wherein R¹ is Trifluoromethyl and Y is Phenyl)

A solution of phenylacetylene (10 mmol) in tetrahydrofuran (30 ml) is cooled to −72° C. and n-butyl lithium in tetrahydrofuran (1 mmol) is added. To this solution is added a solution of S-(trifluoromethyl)phenyl-4-fluorophenyl-3-nitrophenylsulfonium triflate (12 mmol) in THF (10 ml). The resulting mixture is stirred under a nitrogen atmosphere for 5 h. The solvent is removed under reduced pressure and the product is purified by column chromatography.

EXAMPLE 4

Preparation of 2-Isoxazolines (Compounds of the Formula IX).

A solution of the oxime of the formula III (5 mmol) in methanol (15 ml) is heated to 30–40° C. Chloramine-T (1.45 g, 5 mmol) is then added, and the contents are heated to reflux. The solvent is removed in vacuo and the residue obtained is extracted with dichloromethane (100 mL), washed with 1M NaOH, brine and then dried. Removal of the solvent under reduced pressure yields the nitrile oxide. The nitrile oxide (5 mmol) is added to the alkene of the formula X (5 mmol) in ethanol (50 ml), and the resulting mixture is refluxed for 3 h. Diethyl ether is added to the cooled reaction mixture. The resulting mixture is washed with brine and water. Concentration under reduced pressure gives the compound of the formula IX. The product can be further purified by recrystallization from suitable recrystallization solvents, e.g., methanol.

EXAMPLE 5

Cyclooxygenase Inhibitory Assay

Cyclooxygenase activity of ovine COX-1 (Oxford Biomedical Research Inc.) and human recombinant COX-2 (Oxford Biomedical Research Inc.) are assayed by a thin layer chromatography (TLC) method as follows. All inhibitors are dissolved in dimethyl sulfoxide to a stock solution of 5 mM. Human recombinant COX-2 (3 units) or ovine COX-1 (15 units) is incubated with inhibitors at several concentrations in a solution containing 100 mM Tris-HCl, pH 7.8, 500 μM phenol and hematin for 90 to 120 minutes at room temperature (24° C.). In controls, equal volumes of DMSO without drug are added to the incubation mixture. After incubation for 90–120 minutes, [1–$^{14}$C]arachidonic acid (50 μM, 51mCi/mmol) (DuPont NEN) is added and incubated at 37° C. for 2 minutes. The reaction is terminated by extraction with 1 mL of ethyl acetate. The ethyl acetate layer is transferred into a fresh tube and evaporated to dryness in a vacuum dryer. The contents of the tubes are reconstituted in 20 mL of ethyl acetate, spotted on a TLC plate (J. T. Baker, Phillipsburg, N.J.) and developed in a mobile phase containing chloroform/methanol (95:5) at 4° C. Radiolabeled prostanoid compounds (the products of COX enzymatic reaction with radiolabeled arachidonic acid substrate) are quantitated with a radioactivity scanner (Fuji, Phosphorimager). The percentage of total products observed at different inhibitor concentrations is divided by the percentage of the products observed for protein samples pre incubated for the same time with DMSO.

EXAMPLE 6

Soft Agar Assay

Compounds of the formula IX are assayed for inhibition of growth of DLD-1 cells in soft agar. DLD1 cells are human colorectal carcinoma cells that overexpress COX-2. DLD-1 cells grow in soft agar and form tumors in nude mice. The soft agar assay is performed as follows. A layer of bottom agar (8% noble agar) is placed onto 60 mm² tissue culture dishes. The tumor cells are trypsinized from normal growth flasks while in exponential growth. The cells are counted by using a hemacytometer and $1.0 \times 10^5$ cells are placed into the top agar mixture containing growth medium, 4% noble agar and various concentrations of drugs. The concentration range is normally between 10 μM to 75 μM. The cells are not refed during the assay system; therefore, the cells are treated with one dose of the agents. The plates are stained 20 days later with a 0.05% (w/v) nitroblue tetrazolium solution (which stains only viable cells) for 48 hours. A comparison of the percent of cell colonies remaining in the drug treated cells is made relative to the untreated cells.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A compound of the formula IX (IX)

wherein $R^1$ is selected from the group consisting of hydrogen, trihalomethyl, $C_1$–$C_6$ alkyl, and a group of the formula II (II)

wherein
$R^3$ and $R^4$ are independently selected from the group consisting of hydrogen, amino, halogen, hydroxyl, nitro, $C_1$–$C_6$ alkyl, $C_1$–$C_6$ alkoxy, carboxy, $C_1$–$C_6$ trihaloalkyl, cyano, alkylsulfonyl, sulfamyl, phosphonato, and hydroxyalkyl;
Y is a group of the formula wherein
$R^2$ is selected from the group consisting of $C_1$–$C_6$ alkyl, $C_1$–$C_6$ alkanoylamino and amino; and
$R^5$ is selected from the group consisting of hydrogen, amino, halogen, hydroxyl, nitro, $C_1$–$C_6$ alkyl, $C_1$–$C_6$ alkoxy, carboxy, $C_1$–$C_6$ trihaloalkyl, cyano, phosphonato, and hydroxyalkyl; and
Z is selected from the group consisting of substituted and unsubstituted carbocylic aromatic systems and heteroaryl; or
a pharmaceutically acceptable salt thereof.

2. The compound of claim 1, wherein $R^5$ is H.

3. The compound of claim 1, wherein $R^1$ is $C_1$–$C_6$ alkyl.

4. The compound of claim 3, wherein $R^1$ is methyl.

5. The compound of claim 1, wherein $R^2$ is amino.

6. The compound of claim 1, wherein Z is substituted or unsubstituted heteroaryl.

7. The compound of claim 6, wherein Z is selected from the group consisting of substituted and unsubstituted indolyl, furyl, thienyl, pyridyl, benzofuryl, benzothienyl, imidazolyl, pyrazolyl, thiazolyl, benzothiazolyl, quinolinyl, and 4-(2-benzyloxazolyl).

8. The compound of claim 1, wherein $R^2$ is $C_1$–$C_6$ alkanoylamino.

9. The compound of claim 8, wherein $R^2$ is n-propionylamino.

10. A pharmaceutical composition comprising a pharmaceutically acceptable carrier and a compound according to claim 1, or a pharmaceutically acceptable salt thereof.

11. A process for the preparation of a compound of the formula IX (IX)

wherein $R^1$ is selected from the group consisting of hydrogen, trihalomethyl, $C_1$–$C_6$ alkyl, and a group of the formula II (II)

wherein
$R^3$ and $R^4$ are independently selected from the group consisting of hydrogen, amino, halogen, hydroxyl, nitro, $C_1$–$C_6$ alkyl, $C_1$–$C_6$ alkoxy, carboxy, $C_1$–$C_6$ trihaloalkyl, cyano, alkylsulfonyl, sulfamyl, phosphonato, and hydroxyalkyl;
Y is a group of the formula wherein
R² is selected from the group consisting of $C_1-C_6$ alkyl, $C_1-C_6$ alkanoylamino and amino; and
R⁵ is selected from the group consisting of hydrogen, amino, halogen, hydroxyl, nitro, $C_1-C_6$ alkyl, $C_1-C_6$ alkoxy, carboxy, $C_1-C_6$ trihaloalkyl, cyano, phosphonato, and hydroxyalkyl; and
Z is selected from the group consisting of substituted and unsubstituted carbocylic aromatic systems and heteroaryl;
the process comprising: contacting an oxime of the formula III (III)

with an oxidizing agent and reacting the resulting nitrile oxide with an alkene of the formula X

(X)

12. The process of claim 11, wherein R⁵ is H.
13. The process of claim 11, wherein R¹ is $C_1-C_6$ alkyl.
14. The process of claim 13, wherein R¹ is methyl.
15. The process of claim 11, wherein R² is amino or n-propionylamino.
16. The process of claim 11, wherein Z is substituted or unsubstituted heteroaryl.
17. The process of claim 16, wherein Z is selected from the group consisting of substituted and unsubstituted indolyl, furyl, thienyl, pyridyl, benzofuryl, benzothienyl, imidazolyl, pyrazolyl, thiazolyl, benzothiazolyl, quinolinyl, and 4-(2-benzyloxazolyl).
18. The process of claim 11, wherein R¹ is $C_1-C_6$ alkyl and the alkene of the formula X is prepared by a process comprising:

(a) condensing a substituted phenyl aldehyde of the formula XI

Y—CHO      (XI)

with nitromethane at a temperature between 75 to 118° C. to give a compound of the formula XII (XII)

and (b) treating the compound of the formula XII with one of:
(i) at least 3 molar equivalents of triethylborane, wherein R¹ is ethyl; or
(ii) at least 3 molar equivalents triethylborane and about 6 to about 20 molar equivalents of an alkyl iodide of the formula XIII

R¹—I      (XIII).

19. The process of claim 18, wherein Y is 4-sulfamylphenyl or n-propionylamino-phenylsulfonyl.
20. The process of claim 19, wherein R¹ is methyl.
21. The process of claim 11, wherein R¹ is trifluoromethyl and the alkene of the formula X is formed by a process comprising:

(a) treating an alkyne of the formula VII (VII)

with iodine in the presence of copper iodide to form a diiodo alkene of the formula XIV (XIV)

(b) reacting the diiodo alkene of the formula XIV with $FSO_2CF_2CO_2CH_3$; and (c) reducing the product of step (b) to give the alkene of the formula X wherein R¹ is trifluoromethyl.

22. The process of claim 21, wherein the reduction in step (c) comprises treatment with zinc/silver acetate.

* * * * *